United States Patent [19]

Wade et al.

[11] Patent Number: 4,979,945
[45] Date of Patent: Dec. 25, 1990

[54] SYRINGE NEEDLE PROTECTOR AND REMOVER

[76] Inventors: Steven E. Wade, Rte. 1, Box 191 B, Hinton, W. Va. 25951; Silas M. Preston, 224 N. Court St., Lewisburg, W. Va. 24901

[21] Appl. No.: 224,468

[22] Filed: Jul. 26, 1988

[51] Int. Cl.⁵ .............................................. A61M 5/32
[52] U.S. Cl. .................................. 604/192; 604/263; 248/229; 248/231.7; 248/316.7; 206/365
[58] Field of Search ..................... 604/110, 192, 263; 206/366, 365; 248/229, 231.7, 231.3, 316.7

[56] References Cited

U.S. PATENT DOCUMENTS

| | | | |
|---|---|---|---|
| 2,645,325 | 7/1953 | Petit | 248/231.3 |
| 2,709,563 | 5/1955 | Starkey | 248/231.3 |
| 2,843,196 | 7/1958 | Schauer | 248/231.7 |
| 2,854,976 | 10/1958 | Heydrich | 604/263 |
| 3,021,942 | 2/1962 | Hamilton | |
| 4,211,380 | 7/1980 | Lillegard et al. | 248/229 |
| 4,430,082 | 2/1984 | Schwabacher | |
| 4,485,918 | 12/1984 | Mayer | |
| 4,559,042 | 12/1985 | Votel | |
| 4,573,975 | 3/1986 | Frist et al. | |
| 4,596,562 | 6/1986 | Vernon | |
| 4,610,667 | 9/1986 | Pedicano et al. | |
| 4,629,453 | 12/1986 | Cooper | |
| 4,659,330 | 4/1987 | Nelson et al. | |
| 4,717,386 | 1/1988 | Simmons | 604/192 |
| 4,846,803 | 7/1989 | Emerson | 604/263 |

FOREIGN PATENT DOCUMENTS 1240228 5/1967 Fed. Rep. of Germany .

Primary Examiner—C. Fred Rosenbaum
Assistant Examiner—Mark O. Polutta
Attorney, Agent, or Firm—Mathews, Woodbridge & Collins

[57] ABSTRACT

A syringe needle cap resheathing and removal apparatus is capable of single-handedly resheathing and removing needle caps of three different standard needle cap shapes. The apparatus can be fastened with an over-center clamp to a patient's bed rail or other convenient location within a hospital. Three needle cap stations reachable by a common access gap in the apparatus correspond to three standard types of needle caps. The gap is angled to the horizontal to permit convenient visual and mechanical access to the respective needle cap operational stations. The apparatus can be rotated relative to the attachment of the clamp for the convenience and preference of the nurse or doctor.

14 Claims, 8 Drawing Sheets

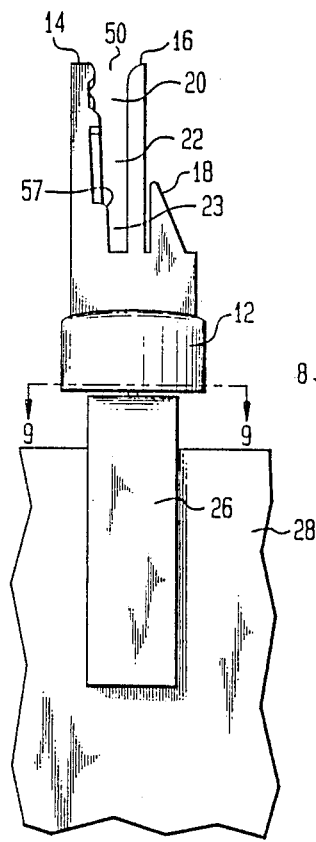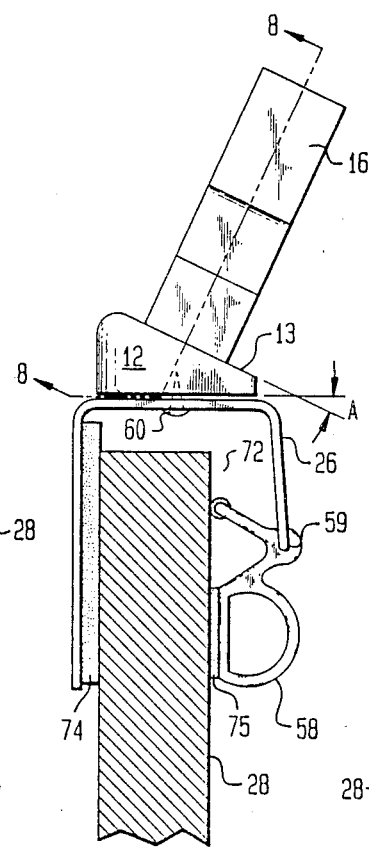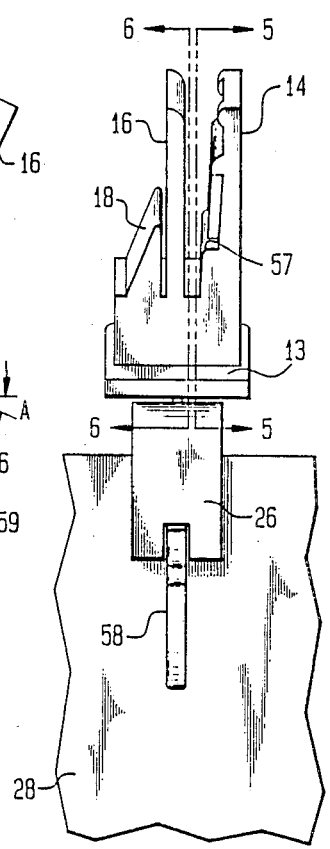

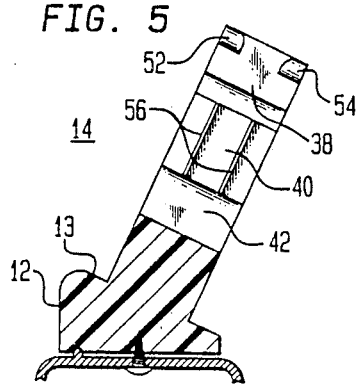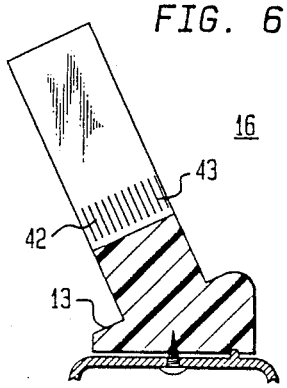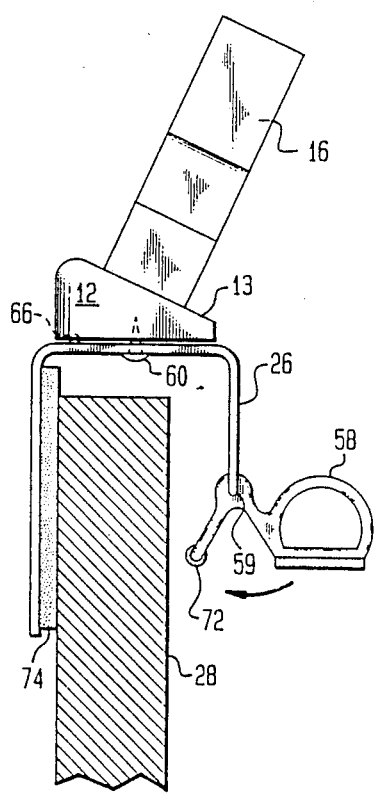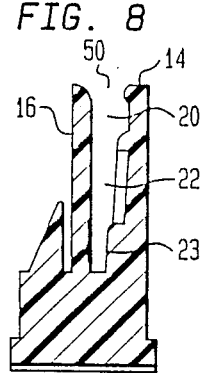

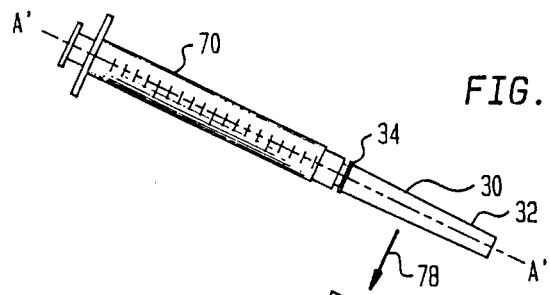
FIG. 11A
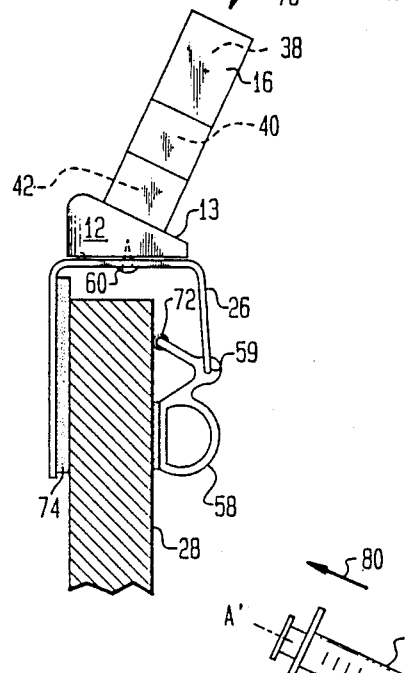
FIG. 11B
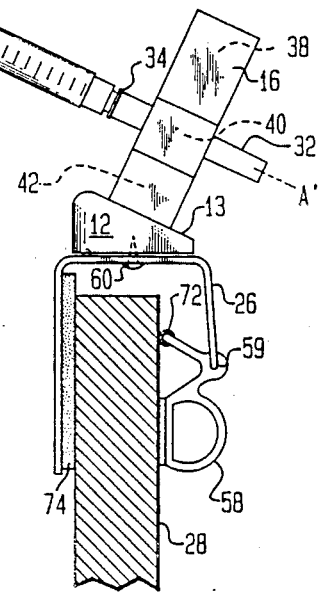

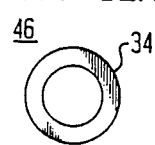 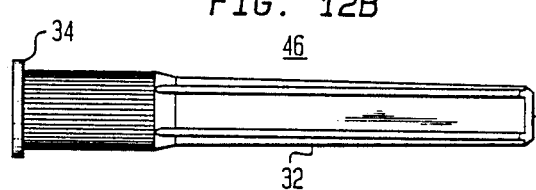 
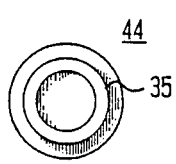 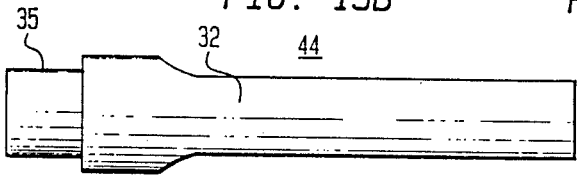 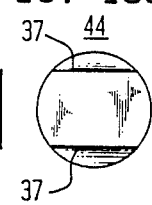
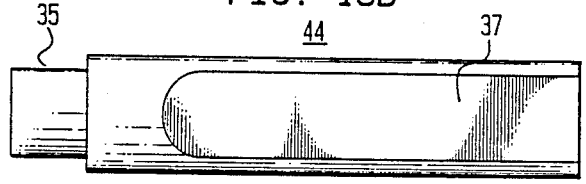
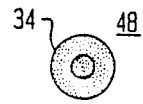 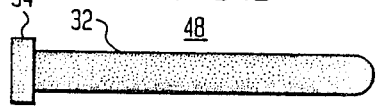 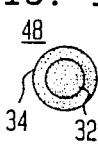

SYRINGE NEEDLE PROTECTOR AND REMOVER

BACKGROUND OF THE INVENTION

1. Field of the Invention

This invention relates to a device for safely resheathing and removing syringe needle caps.

2. Description of the Related Art

The problem of hospital personnel being injured by unsheathed syringe needles has persisted since the initial use of hypodermic syringes. Until recently, such injuries have ranged from the inconvenience of a "needle stick" to the risk of contracting a serious disease such as hepatitis. However, with the advent of the disease AIDS, each common occurrence of an accidental puncture wound with a contaminated needle may represent a life threatening situation for the injured hospital employee.

One approach to solving this problem has been an attempt to safely assist the nurse or physician in replacing the needle cap provided by the manufacturer. U.S. Pat. No. 4,485,918 describes a funnel-type design to protect the hand holding the cap while replacing the cap on the used needle. This device requires the use of both hands, one to hold the apparatus containing the needle cap and the other to hold the syringe with the exposed contaminated needle. Each different needle cap type and size requires its own customized apparatus. Further, the device does not provide a means for removing the needle cap. While needle cap removal injuries are less frequent than resheathing problems, accidental puncture wounds occur with regular frequency in this procedure as well.

U.S. Pat. No. 4,610,667 describes another funnel structure designed to permit resheathing the used needle. The apparatus is then disposed with the used needle and its replaced cap. An apparatus that must be discarded after a single use significantly increases the cost of each injection. The apparatus requires the use of both hands in the resheathing operation. Once the cap has been replaced on the needle, it cannot easily be removed from the device. Often, hospital procedure requires a nurse to fill syringes, replace the needle caps, then administer the injections at a later time. Again, each needle cap type requires its own size funnel sheathing apparatus and no means for cap removal is provided.

U.S. Pat. No. 4,596,562 describes a hand-held v-slotted plate-like member for cap replacement. The device includes three holes as an alternative method for holding and resheathing needle caps. This device also requires the use of both hands to replace the needle cap. Most needle cap injuries occur while rushing to resheath a contaminated needle. An apparatus requiring the use of both hands does not provide fail-safe resheathing procedures. Similarly, as in the other cited patents, no provision for removing the caps is desired.

Of possible general relevance to the invention are U.S. Pat. Nos. 3,021,942; 4,430,082; 4,559,042; 4,573,975; 4,629,453; and German Patent No. 1,240,228. U.S. Pat. No. 4,659,330, is representative of the above cited patents. This approach to solving the problem has been to redesign the needle cap itself rather than use the caps provided by needle manufacturers. A needle cap must be used only once and then discarded. Complex designs require manufacturing changes or repackaging changes by needle manufacturers. Further, such complex designs which can be used only once, defeat the economic advantages of disposable needles and syringes.

A practical solution to the problem of handling three standard types of needle caps provided by needle manufacturers and single handedly resheathing and removing the needle caps is not found in the prior art.

SUMMARY OF THE INVENTION

Briefly described, the invention comprises a needle cap removal and resheathing apparatus that is readily attachable to a hospital bed, medication cart, or mountable in a location requiring frequent use of hypodermic syringes such as blood labs, or operating rooms.

The base of the apparatus is fitted with a clamp that rigidly mounts the device to a stationary object such as a hospital bed rail. The base is provided with a swivel so that the apparatus can be adjusted relative to the clamp thereby accommodating the preference of the nurse or doctor. A detent system permits the base to be adjusted to a plurality of positions while providing positioning stability. The base is angled to the horizontal thereby permitting visual and mechanical access to three needle removal and resheathing stations that correspond to three standard needle cap types. A first and second arm extends perpendicular from the base to form a gap. To remove a needle cap, the operator holds the syringe with one hand approximately parallel to the base. The needle cap is placed in the gap, and moved downwardly towards the base, until the gap between the arms corresponds to that particular needle cap type. Then the needle cap is jam-fitted into that station of the gap. The two arms are resilient permitting the cap to be firmly held while the syringe and its needle are removed. A third arm is provided adjacent to one of the other arms to prevent the first and second arms from being overflexed.

In order to resheath the cap, which can be held in the apparatus while the syringe is in use, the syringe is held approximately parallel to the base and in line with the needle cap. The syringe with the contaminated needle is moved with one hand toward the cap held in the apparatus. Once the needle is inserted completely in the needle cap, the syringe is lifted upwardly, away from the base.

Each of the three stations of the gap formed between the two arms is designed to remove or resheath one of three common types of needle caps. Needle caps, when held between the first and second arms with their long axis approximately parallel to the base of the apparatus, can easily be moved perpendicularly away from the base but will be held fast if the cap is moved in a direction parallel to the base. Flexibility of the arms permits different cap sizes to be removed or resheathed.

These and other features of the invention will be more fully understood by reference to the following drawings.

BRIEF DESCRIPTION OF THE DRAWINGS

FIG. 2 is a front elevational view of the preferred embodiment of the apparatus.

FIG. 3 is a right side elevational view of the preferred embodiment of the apparatus.

FIG. 4 is a rear elevational view of the preferred embodiment of the apparatus.

FIG. 5 is a cross-sectional view of the preferred embodiment of the apparatus illustrated in FIG. 4.

FIG. 6 is a cross-sectional view of the preferred embodiment of the apparatus illustrated in FIG. 4.

FIG. 7 is right side elevational view of the apparatus showing the overcenter-type clamp in the unlocked position.

FIG. 8 is a cross-sectional view of the preferred embodiment of the apparatus illustrated in FIG. 3.

FIGS. 11A–11D illustrate the preferred embodiment of the apparatus in the process of removing and resheathing a typical needle cap.

FIGS. 12A–12C illustrate the most common type of needle cap.

FIGS. 13A–13C illustrate the multiple sample type of needle cap.

FIGS. 14A–14C illustrate a "Demerol" type of needle cap.

DETAILED DESCRIPTION OF THE INVENTION

During the course of this description, like numbers will be used to identify like elements according to the different views that illustrate the invention.

Figure 1:
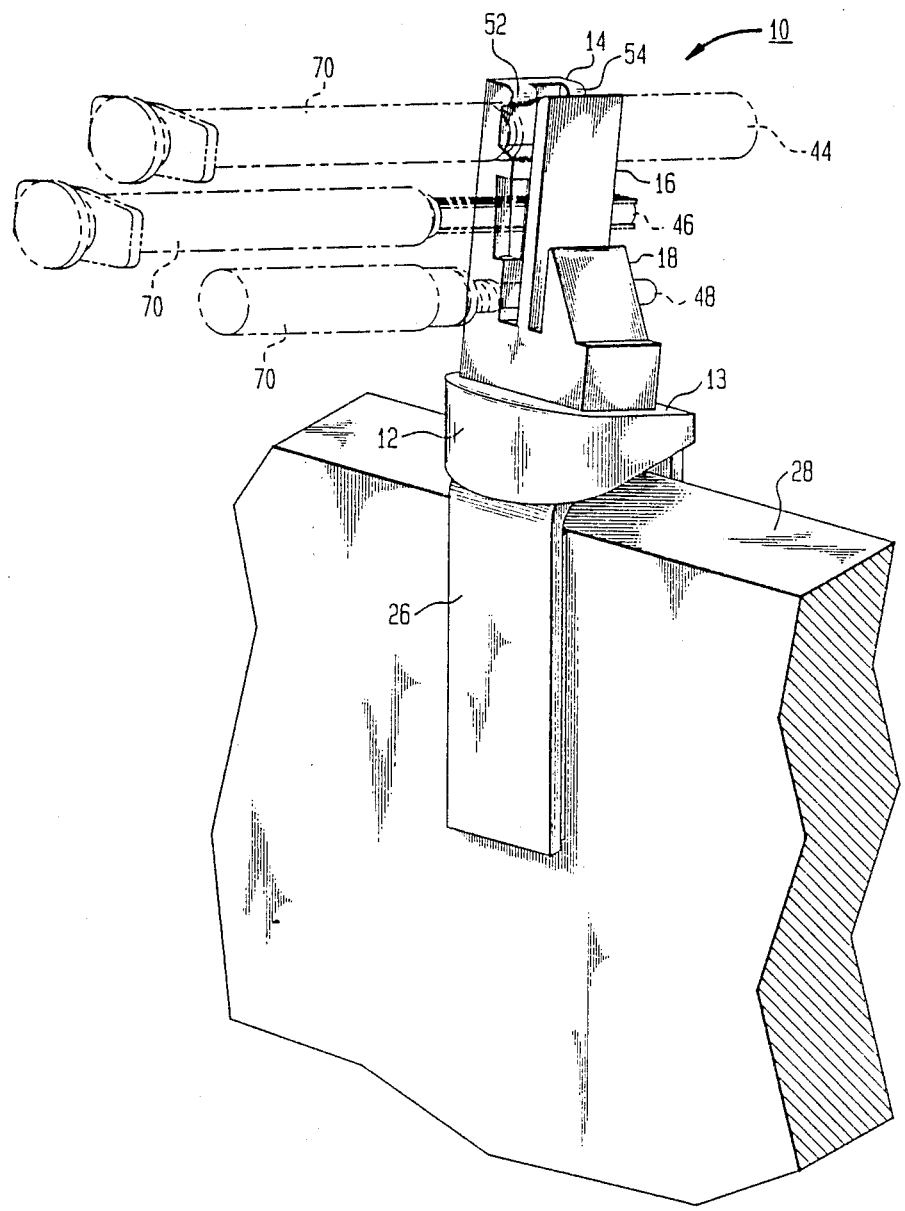
FIG. 1 is a perspective view of the apparatus shown with three standard needle caps and their corresponding syringes.

The preferred embodiment of the invention 10 is illustrated in FIG. 1 in the context of three standard needle caps, a multiple sample type of needle cap 44, one of the most common types of needle caps 46, a Demerol type needle cap 48 and their corresponding syringes 70. Clamp 26 attaches the invention 10 to bed rail 28. Clamp 26 could also be used to attach invention 10 to a medication cart or other convenient locations within a hospital. Clamp 26 is preferably fabricated out of metal but plastic, such as nylon, could also be used. Pivotally mounted on clamp 26 is base 12. Affixed and perpendicular to surface 13 is first arm 14. Arm 14 is permanently attached to and integral with surface 13, however, an alternative embodiment has at least a portion of arm 14 capable of being removed which will be more fully explained in FIG. 10. Adjacent to first arm 14 is second arm 16 which is likewise affixed and perpendicular to surface 13. A third arm 18 is similarly attached to the surface 13. Arms 14, 16, 18 and base 12 are preferably fabricated out of a resilient material such as nylon.

First arm 14 and second 16 will flex apart from each other when a needle cap, for example, cap 44, is placed between the two arms. Third arm 18 acts as a stop to insure that arms 14, 16 cannot be overflexed.

FIG. 2 illustrates opening 50 where a needle cap is inserted between first arm 14 and second arm 16. First gap 20 is the region designed for removal and resheathing of the multiple sample type of needle cap 44. The preferable width of gap 20 is approximately 0.33 inches. Second gap 22 is the region designed for removal and resheathing the most common type of needle cap 46. The preferable width of gap 22 is approximately 0.19 inches at the top, tapering down to 0.16 inches at the bottom. The distance from the top of gap 22 to the bottom of gap 22 is approximately 0.38 inches. Third gap 23 is the region designed for removal and resheathing a Demerol-type needle cap 48. The preferable width of gap 23 is approximately 0.13 inches.

FIG. 3 illustrates acute angle A between surface 13 of base 12 and the horizontal thereby positioning first arm 14 and second arm 16 in a convenient orientation so that the respective needle caps may be inserted approximately parallel to surface 13. Angle A may range between 20 and 25 degrees, preferably 22.5 degrees. Base 12 is attached to clamp 26 by swivel pin 60, thus enabling base 12 to rotate about clamp 26.

FIG. 5 illustrates a cross-sectional view of invention 10, as shown in FIG. 4, illustrating the surface of arm 14 that faces arm 16 thereby providing the three needle cap stations for removing and resheathing the three needle cap types, 44, 46, and 48. First needle cap operating station 38 corresponds to the needle cap type 44. First ledge 52 and second ledge 54 are attached to arm 14 and extend into gap 20 approximately 0.13 inches, parallel to each other on opposite ends of arm 14. The longer portion of multiple use needle cap 44 snap into gap 20 is held firmly by first ledge 52 and second ledge 54. When barrel 32 of needle cap 44 is jam-fitted in gap 20, cap 44 is then grasped for removal or resheathing.

Second needle cap station 40, shown in FIG. 5, is used for the most common type of needle cap 46. Parallel blades 56 extend outwardly from the surface of arm 14 perpendicular to surface 13. The distance between the two blades is not critical but preferably should be at least 0.25 inches. When blades 56 are dull, they can be replaced which is explained more fully in FIG. 10. When a cap 46 is jam-fitted between arms 14 and 16, blades 56 engage the plastic surface of cap 46 holding cap 46 fast in a direction relative to its long axis while permitting cap 46 to be easily moved away from base 12.

Third needle cap station 42 includes a smooth surface on arm 14. FIG. 6 illustrates a cross-sectional view of invention 10, as shown in FIG. 4, showing the surface of arm 16 facing arm 14. FIG. 6 illustrates the corresponding needle cap operating station 42 of arm 16. A plurality of channels 43 on the surface of arm 16, approximately perpendicular to surface 13, will grip needle cap 48 when it is jam fit between arm 14 and arm 16. The number of channels is not critical but preferably should extend the width of arm 16, with each channel approximately 0.02 inches deep.

FIG. 7 illustrates the preferred embodiment of clamp 26 with an overcenter locking mechanism. The preferred material for construction would be spring steel having a tensile strength such that unlatching invention 10 from a hospital bedboard which is approximately 0.75 inches wide would require no greater than a seven pound pull by the operator. A screw-type clamp can also be used. Shown in the unlocked position in FIG. 7, finger lever 58 is rotated in the direction of arrow 86 about pivot point 59. Roller 72 engages the surface of bed rail 28 causing clamp 26 to spring away from bed rail 28. Finger lever 58 is rotated until finger lever 58 engages bed rail 28 with pad 75 coming to rest against the bed rail 28, thereby locking the invention 10. Pad 74 and 75 are preferably fabricated out of non-marring material such as rubber permitting clamp 26 to be tightly locked without scratching or otherwise damaging the surface of bed rail 28. The locked position of clamp 26 is shown in FIG. 3.

FIG. 8 illustrates that arms 14, 16, 18 and base 12 form an integral unit.

Figure 9A:
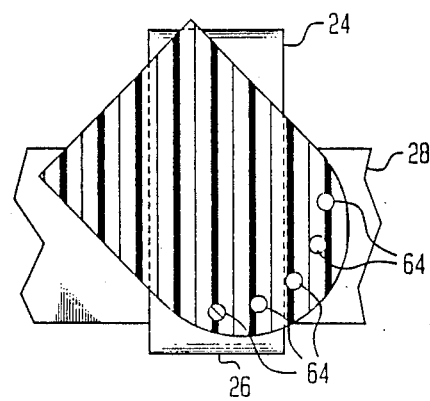
FIGS. 9A–9C are cross-sectional views of the preferred embodiment of the apparatus illustrated in FIG. 2 showing the base in different positions relative to the overcenter-type clamp.
Figure 9B:
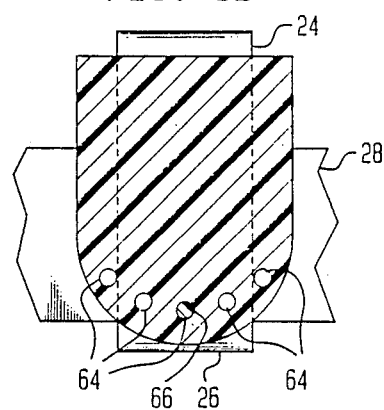
Figure 9C:
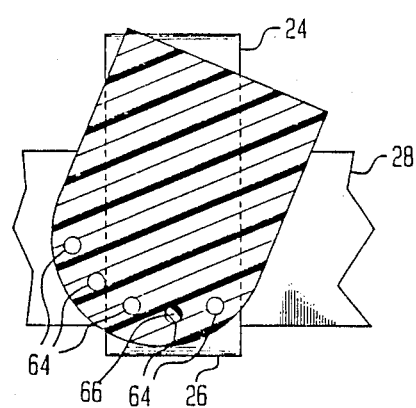

FIGS. 9A–9C, a cross-sectional view through base 12 as shown in FIG. 2, illustrate that the base 12 can be rotated relative to clamp 26. Swivel platform 24 of clamp 26 is fitted with a projection 66, best viewed by referring to FIG. 7. Projection 66 can be a spring-loaded pin or preferably an integral projection of swivel platform 24 which can engage one of the plurality of detent recess stops 64. The number of stops 64 is not critical but should be sufficient to meet the preferences of medical personnel. Six stops 64 are preferable.

Figure 10:
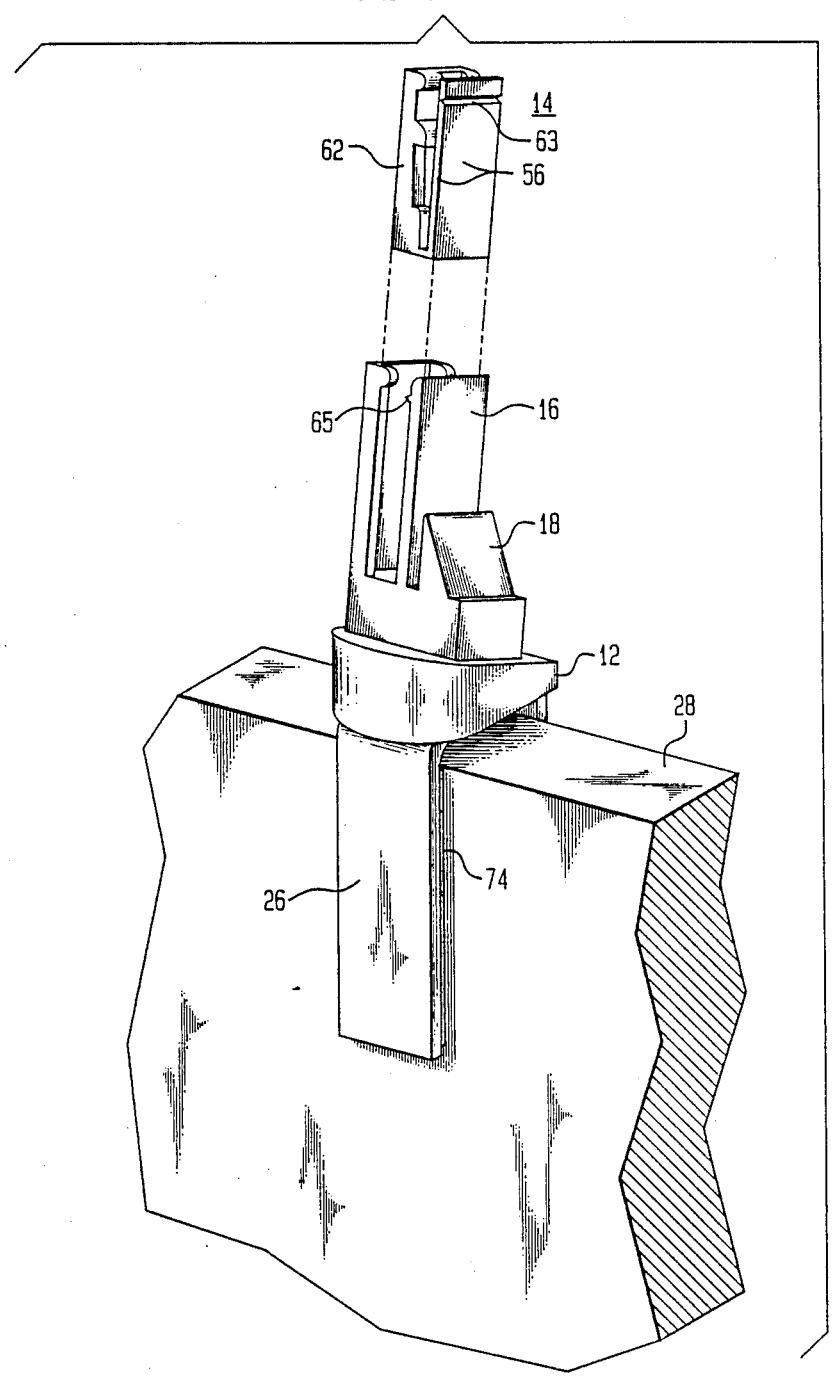
FIG. 10 is an exploded view of the preferred embodiment showing the removal of the arm insert.

FIG. 10 illustrates an alternative embodiment having at least a portion of arm 14 as an arm insert 62. In this manner, blades 56 can be replaced through slots in the back surface of arm insert 62 with the sharp edges of blades 56 facing arm 16. Arm insert 62 is fastened to base 12 or the third needle cap operation station 42 of arm 14.

FIGS. 11A and 11B show invention 10 in operation to remove a needle cap. Needle cap type 46 is shown but the operation is essentially the same as with the other two types. Syringe 70 with its needle cap 30 is held above invention 10 approximately aligned along axis A—A'. Axis A—A' is approximately through the long axis of syringes 7 and their corresponding respective needle caps 44, 46, and 48 so that when the needle caps 44, 46, and 48 are placed between first arm 14 and second arm 16, the long axis of the needle caps is approximately parallel to surface 13. The syringe is moved downwardly, in the direction of the arrow 78, towards second needle cap station 40, until needle cap 30 is jam-fitted into the region of station 40 that corresponds to that size needle cap.

FIG. 11B shows the syringe a its jam fit position approximately aligned along axis A—A'. The syringe with the unsheathed needle is moved approximately along axis A—A' in the direction of the arrow 80.

Figure 11C:
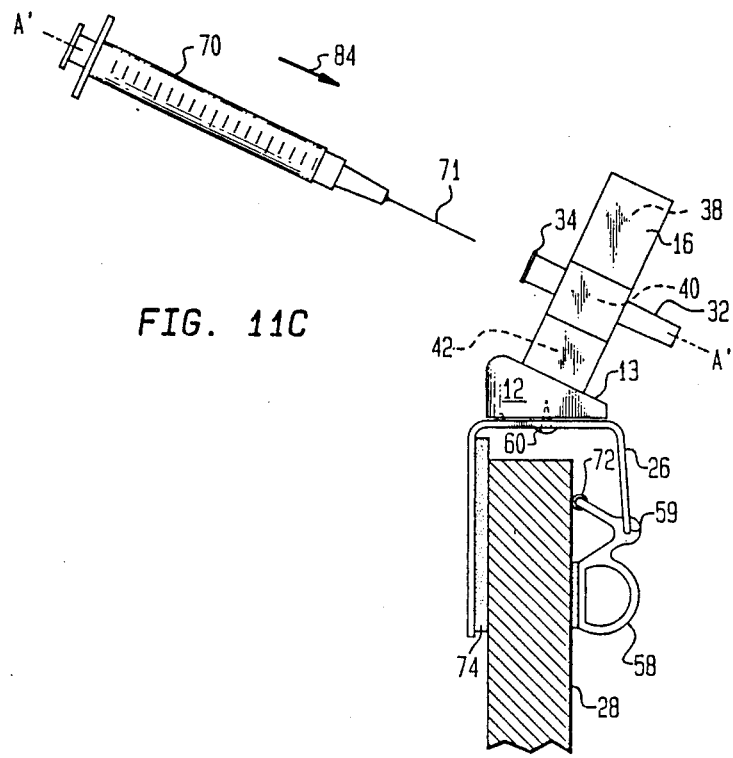
Figure 11D:
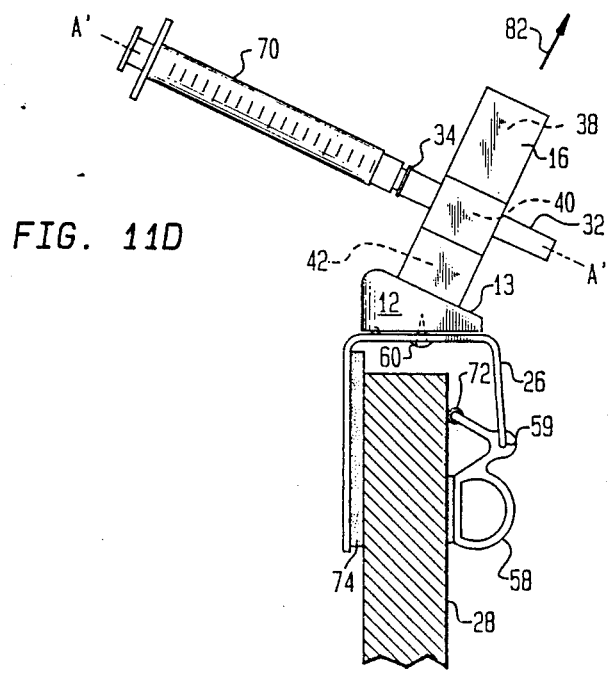

FIGS. 11C and 11D show invention 10 in operation to resheath a needle, either one that is contaminated or one that is to be used at a later time. Syringe 70 with needle 71 attached is held approximately aligned with axis A—A'. Axis A—A' is shown in parallel to surface 13 and is approximately co-incident with the long axis of the needle cap barrel 32 of needle cap 30. Once aligned, the syringe 70 is moved in the direction of arrow 84 toward needle cap 30, until needle 71 is completely within needle cap 30 and flange 34 is in its fully engaged position.

FIG. 11D shows the syringe 70 with its needle cap 30 resheathed. Then the syringe is moved away from base 12 in the direction of the arrow 82 with needle cap 30 returned to sheathed position.

FIGS. 12A–12C show the most common needle cap type 46. FIG. 12A illustrates the open end of ca 46 surrounded by flange 34. When needle is fully within cap 46, flange 34 firmly engages syringe 70. FIGS. 12B and 12C show barrel 32 of cap 46 having four longitudinal ribs. Blades 56 of station 40 engage one or more of the ribs to hold the cap fast in direction coincident with the long axis of cap 46. However, cap 46 is easily released in the direction of its short axis.

A multiple sample type of needle ca 44 is shown in FIGS. 13A–13C. Collar 35 in FIG. 13A fits over needle 71 which has both ends sharp and a threaded mechanism in middle of needle 71 for changing vacuum syringes (not shown). Barrel 32 of cap 44, shown in FIGS. 13B and 13C, has two flat surfaces 37 opposite to one another. Surfaces 37 engage first ledge 52 and second ledge 54 in station 38 to remove cap 44.

A "Demerol" type of needle cap is illustrated in FIGS. 14A–14C. Cap 48 may have a well-defined flange 34 as shown or the end may just be slightly flared to receive the needle 71 and its syringe 70. Circular barrel 32 of cap 48 as shown in FIGS. 14B and 14C is held by the channels 43 of station 42 to permit removal or resheathing.

The invention 10 just described has several distinct advantages over prior art devices. First, needle caps can be removed or resheathed using one hand only. This permits the operator to keep the other hand well away from the needle or for another purpose such as holding a patient file and eliminates the potential of an accidental puncture wound occurring during the capping or uncapping operation. Secondly, the invention 10 can be mounted in convenient locations throughout the hospital such as patient bed rails, medication carts, operating rooms, blood laboratories, or in any location where frequent use of hypodermic needles is likely. Third blades used for removing and resheathing the most common type of needle cap, are replaceable. Fourth, the invention 10 can be rotated relative to the attachment clamp thereby obtaining the most convenient position for the medical personnel. Fifth, invention 10 is capable of removing and resheathing three of the most common types of needle caps without requiring additional disposal devices which would add to the cost of each injection. Sixth, a needle cap that has been removed can be left in the invention 10 while the syringe is being used, thus eliminating the extra steps of finding the cap and then placing it in a device so that it can be resheathed. Finally, the syringe with its needle cap may be conveniently held by invention 10 to permit medical personnel to attend to any intervening matters without being concerned that the syringe placed on a medication cart or patient's night stand will roll off onto the floor.

While the invention has been described with reference to the preferred embodiment thereof it will be appreciated by those of ordinary skill in the art that modifications can be made to the parts that comprise the invention without departing from the spirit and scope thereof.

We claim:

1. A syringe needle cap removal and resheathing apparatus comprising:
 a base;
 a first arm attached to said base;
 a second arm also attached to said base and separated from said first arm by a needle cap receiving gap having an opening opposite from said base, wherein a needle cap is firmly holdable in said gap when said cap is introduced sidewise into said opening and moved downwardly toward said base until further downward movement substantially stops at which point said syringe can be pulled away from said needle cap, wherein said first and second arms are made of materials that permit them to flex with respect to each other so that a needle cap can jam fit into said gap, and wherein said gap between said first and second arm includes at least a first and a second station for removing and resheathing needle caps of at least a first and a second kind having respectively two different barrel shapes;
 a clamp attached to said base for selectively clamping said apparatus to a stationary object;

a swivel means attached between said clamp and said base for permitting said base to rotate with respect to said clamp;

a third arm attached to said base and located adjacent to one of said other arms to limit the flexing of the arm that it is located adjacent to; and blade means located in at last one of said two stations for cutting into said needle cap as said needle cap is jammed into said gap and for holding onto said needle cap when force is applied to said needle cap perpendicular to said blade means.

2. The apparatus of claim 1 wherein said blade means comprise at least two sharp blades oriented substantially parallel to the long axis of said gap.

3. The apparatus of claim 2 further comprising a third station located in said gap for removing a cap of at least a third kind having a third different barrel size.

4. The apparatus of claim 3 wherein said first and second arms and said base comprise a single integrated unit.

5. The apparatus of claim 4 wherein at least a portion of said first arm comprises a removable insert for carrying said blade means.

6. The apparatus of claim 5 further comprising:
said base includes a plurality of recess stops; and,
said clamp includes a swivel platform with a projection, wherein said projection engages one of said recess stops.

7. The apparatus of claim 6 wherein said base has a surface ranging from 20 to 25 degrees from the horizontal.

8. The apparatus of claim 7 further comprising:
a third station having a plurality of ridges for holding onto said needle cap when said cap is jammed into said gap.

9. The apparatus of claim 8 further comprising:
ledge means located in at least one of said two stations for holding needle cap types having a barrel with two flat opposite surfaces when said needle cap type is jammed into said gap.

10. The apparatus of claim 1 wherein said clamp is an overcenter-type clamp.

11. A syringe needle cap removal and resheathing apparatus comprising:
a base;
a first arm attached to said base;
a second arm also attached to said base and separated from said first arm by a needle cap receiving gap having an opening opposite from said base; and
at least one blade mounted in said gap having means for cutting the surface of a needle cap when said needle cap is introduced into said gap and for holding onto said needle cap to prevent longitudinal movement of said needle cap when force is applied to said needle cap perpendicular to said blade.

12. The apparatus of claim 11 wherein said blade is mounted on the surface of one of said arms.

13. The apparatus of claim 12 wherein a plurality of said blades are mounted in said gap.

14. The apparatus of claim 13 wherein said plurality of blades are parallel to each other.

* * * * *